United States Patent
Cohn et al.

(10) Patent No.: US 8,097,005 B2
(45) Date of Patent: *Jan. 17, 2012

(54) SUTURE SYSTEM

(75) Inventors: William Cohn, Chestnut Hill, MA (US); Thomas P. Mathers, Newbury, MA (US)

(73) Assignees: Beth Israel Deaconess Medical Center, Boston, MA (US); Teleflex Incorporated, Limerick, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/647,657

(22) Filed: Aug. 25, 2003

(65) Prior Publication Data

US 2004/0106949 A1 Jun. 3, 2004

Related U.S. Application Data

(63) Continuation of application No. 09/360,709, filed on Jul. 26, 1999, now Pat. No. 6,610,071.

(51) Int. Cl.
*A61B 17/04* (2006.01)

(52) U.S. Cl. .................................... 606/148; 606/228

(58) Field of Classification Search .............. 606/148, 606/139, 222–228, 144–147, 150, 232; 623/2.11, 623/2.41, 2.36–2.37, 2.1, 2.22

See application file for complete search history.

(56) References Cited

U.S. PATENT DOCUMENTS

| | | | | |
|---|---|---|---|---|
| 2,591,063 A | 4/1952 | Goldberg | | 128/334 |
| 3,762,418 A | 10/1973 | Wasson | | 606/223 |
| 4,164,046 A | 8/1979 | Cooley | | 623/2.36 |
| 4,185,636 A | 1/1980 | Gabbay et al. | | 606/148 |
| 4,405,044 A | 9/1983 | Flower et al. | | 206/44.12 |
| 4,549,545 A | 10/1985 | Levy | | 128/335 |
| 4,566,607 A | 1/1986 | Smith | | 221/155 |
| 4,632,113 A | * 12/1986 | Ablaza | | 606/222 |
| 4,702,250 A | * 10/1987 | Ovil et al. | | 606/148 |
| 4,932,965 A | * 6/1990 | Phillips | | 623/2.11 |
| 5,123,528 A | 6/1992 | Brown et al. | | 206/63.3 |
| 5,207,703 A | 5/1993 | Jain | | 606/232 |
| 5,259,846 A | 11/1993 | Granger et al. | | 606/224 |
| 5,284,293 A | * 2/1994 | Alpern et al. | | 229/122.1 |
| 5,304,184 A | 4/1994 | Hathaway et al. | | 606/148 |
| 5,383,904 A | 1/1995 | Totakura et al. | | 606/228 |
| 5,450,860 A | 9/1995 | O'Connor | | 128/898 |
| 5,593,424 A | 1/1997 | Northrup, III | | 606/232 |
| 5,690,230 A | 11/1997 | Griffith | | 206/555 |
| 5,709,695 A | 1/1998 | Northrup, III | | 606/148 |
| 5,762,458 A | 6/1998 | Wang et al. | | 414/1 |
| 5,792,135 A | 8/1998 | Madhani et al. | | 606/1 |
| 5,797,900 A | 8/1998 | Madhani et al. | | 606/1 |
| 5,807,377 A | 9/1998 | Madhani et al. | | 606/1 |
| 5,813,597 A | 9/1998 | Wakevainen | | 229/122.1 |

(Continued)

FOREIGN PATENT DOCUMENTS

EP 0 494 636 7/1992

(Continued)

*Primary Examiner* — Gary Jackson
*Assistant Examiner* — Lindsey Bachman
(74) *Attorney, Agent, or Firm* — Weingarten, Schurgin, Gagnebin & Lebovici LLP

(57) ABSTRACT

A suture system includes a plurality of double-stranded needles connected in sequence with a single-stranded needle at each end. The double-stranded suture needles incorporates two suture strands into a single needle. The suture system of the present invention facilitates the implantation of valve prostheses.

34 Claims, 9 Drawing Sheets

U.S. PATENT DOCUMENTS

| | | | | |
|---|---|---|---|---|
| 5,814,096 | A | 9/1998 | Lam et al. | 623/2 |
| 5,824,064 | A | 10/1998 | Taheri | 623/2 |
| 5,843,126 | A | 12/1998 | Jameel | 606/220 |
| 5,855,583 | A | 1/1999 | Wang et al. | 606/139 |
| 5,860,517 | A | 1/1999 | Gemma, Jr. et al. | 206/63.3 |
| 5,871,489 | A | 2/1999 | Ovil | 606/148 |
| 5,891,160 | A | 4/1999 | Williamson, IV et al. | 606/144 |
| 5,891,195 | A | 4/1999 | Klostermeyer et al. | 623/2 |
| 5,908,452 | A | 6/1999 | Bokros et al. | 623/2 |
| 5,911,036 | A | 6/1999 | Wright et al. | 395/94 |
| 6,610,071 | B1 * | 8/2003 | Cohn et al. | 606/148 |

FOREIGN PATENT DOCUMENTS

| | | |
|---|---|---|
| EP | 0 554 653 | 8/1993 |
| SU | 513696 * | 5/1976 |
| SU | 513696 | 6/1976 |
| SU | 827047 | 1/1979 |
| SU | 827047 | 5/1981 |
| WO | WO 96/04852 | 2/1996 |
| WO | WO 98/29039 | 7/1998 |
| WO | WO 98/53745 | 12/1998 |
| WO | WO 99/60929 | 12/1999 |

* cited by examiner

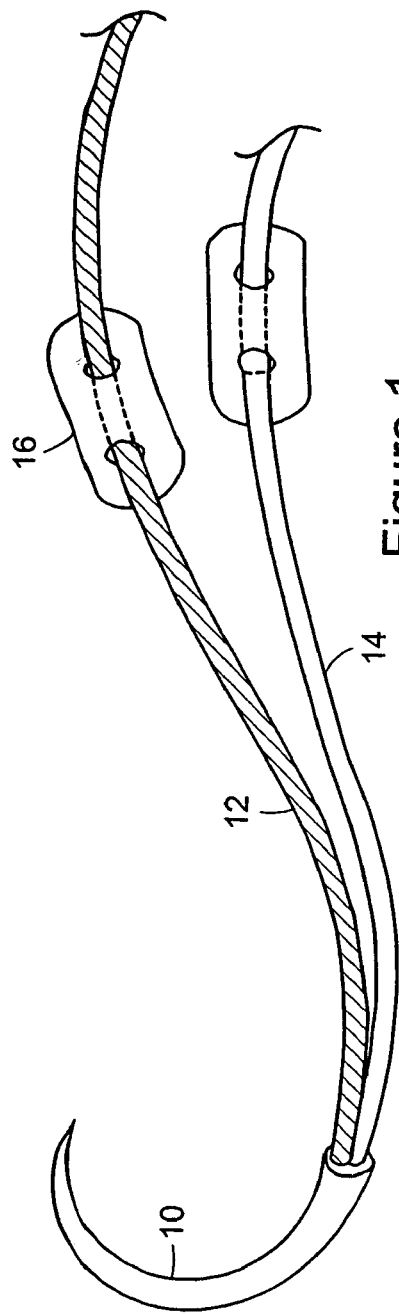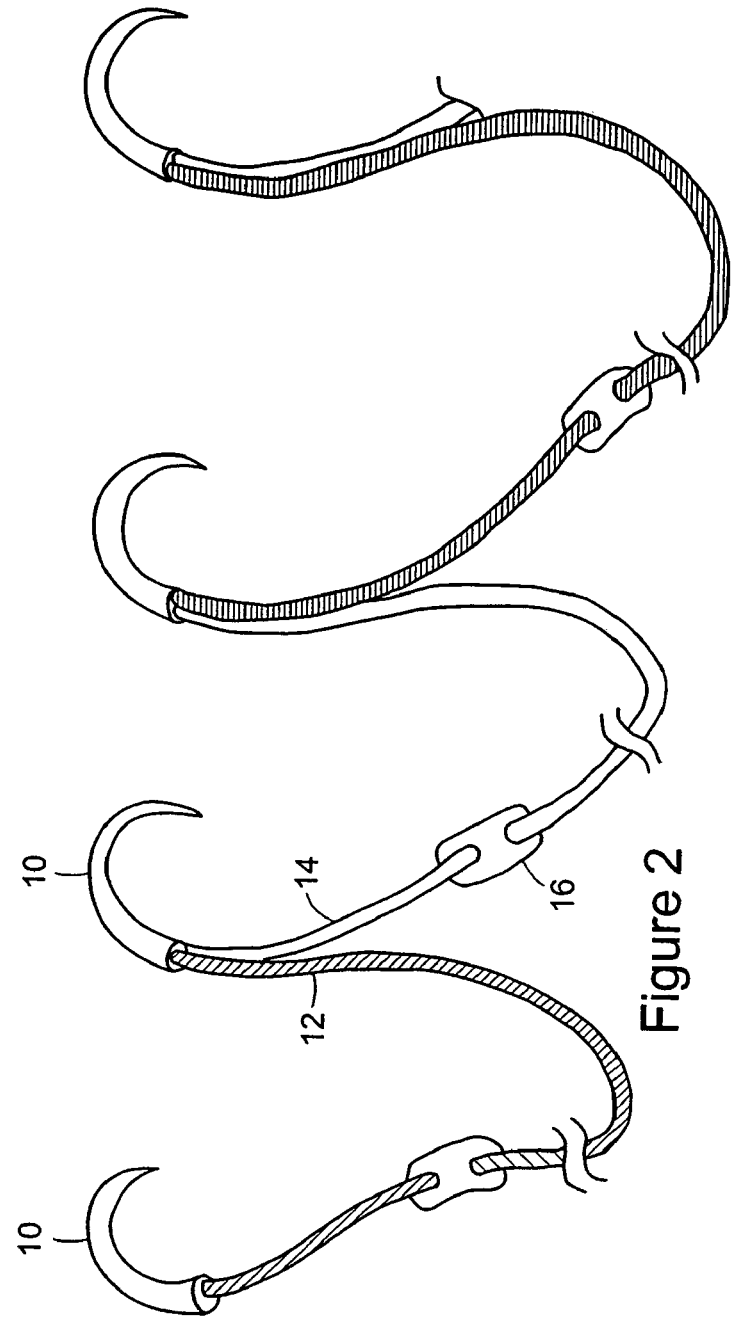

SUTURE SYSTEM

CROSS REFERENCES TO RELATED APPLICATIONS

The present application is a continuation of U.S. patent application Ser. No. 09/360,709, filed Jul. 26, 1999, now U.S. Pat No. 6,610,071.

The entire contents of the above applications are incorporated herein by reference in entirety.

BACKGROUND OF THE INVENTION

By far the most frequently used technique for implantation of prosthetic valves such as aortic and mitral valves is to use pledgeted mattress sutures. The term "mattress" refers to the fact that each suture passes through the fabric suturing ring or cuff of the prosthetic valve and through the tissue to which the prosthesis will be attached at two points separated, for example, by a gap of about 4 to 8 mm and more preferably between about 4 to 6 mm. To facilitate this, the piece of suture material has two surgical needles pre-attached, one at each end. The term "suture" refers to the composite of suture material and needles. The suture material for valve prosthesis implantation is typically made of nonabsorbable polyester. When the two ends of a single suture are tied together, a 4-8 mm segment of the circumference of the valve ring and the circumference of the annulus, (the rim of heart tissue that remains after excision of the dysfunctional native valve, and to which the prosthesis is sutured) are compressed tightly together.

To decrease the likelihood of the suture pulling through the annular tissue as tension is applied during tying, most surgeons use pledgeted sutures. A "pledget" is a small flat absorbent pad used to protect a wound. It is made from a piece of PTFE coated felt from a polyester material, through which both needles of the suture have been passed. The size of the pledget varies with a preferred size of 4×8 mm. Sutures usually come pre-pledgeted from the manufacturer in multi-packs for valve implantation. When pledgeted sutures are used, generally both needles are passed through the annular tissue as the initial step in such a way that the pledget lies in direct contact with the tissue and helps to distribute the force supplied to the 4-8 mm of tissue that lies between the two points of suture penetration. When tied, the annular circumference is compressed between the suturing ring of the prosthesis and the pledget. Multiple sutures are required to create this fluid tight compressive force between the tissue and the prosthesis.

In order to prevent leakage of blood between the prosthetic valve and the tissue annulus post operatively, accurate spacing of the multiple discrete sutures is essential. Tight compression between the tissue and the prosthetic ring is readily achieved if the two ends of the mattressed sutures are tightly tied together. Peri-valvular leakage, when it occurs, is more commonly the result of an excessive distance separating two neighboring pledgets. As such, it is essential to pass the first needle (that is to say, the first of any given pair, the pair consisting of the two ends of a single suture) through the annulus as close as possible to the second suture of the neighboring pair. This must be accomplished, however, without actually piercing the preceding suture. Valve sutures are a braided multifilament material and it is possible to pass one suture around or through the interstices of the neighboring strand. Although not always readily apparent at the time, this passing of one suture through the interstices of the adjacent strand may result in suture breakage when the sutures are tied, or in poor seating of the valve due to unevenly distributed tension.

To ensure that the entire circumference of the prosthesis is seated in the annulus in a fluid tight fashion, multiple sutures are required. If the diameter of the annulus is 29 mm, which is quite common in mitral valve replacement, and the mattress sutures are placed such that each encompasses 5 mm of annulus, approximately 18 discrete mattress sutures are required which involves passing 36 needles initially through the tissue, and subsequently through the suturing ring. As described above, every other stitch is technically more demanding and slightly more time consuming because of the increased precision required to pass extremely close to the preceding suture but without piercing it. As space is often quite limited when working inside the heart, the entire exercise can be very demanding. There is thus a continued need to provide improved suture devices and systems to accommodate small incisions associated with minimally invasive surgery and to simplify procedures for the implantation of prosthetic valves.

SUMMARY OF THE INVENTION

The invention consists of a configuration whereby a plurality of double-stranded needles are connected in sequence with a single-strand needle at each end. Each double-stranded needle incorporates two suture strands or threads on a single needle. In a preferred embodiment, the suture strands can alternate in color. Thus any give pair of needles are connected by a first strand of a first color and the next needle is connected with a second strand of a second color. A plurality of pledgets can be provided on the strands and can be arranged in a "daisy chain" configuration with a single pledget or pad positioned between each pair of needles in the chain.

In a preferred embodiment, the suture system of the present invention may contain several co-braided monofilament suture strands, where two strands of different colors, such as green and white, are co-braided into a single suture strand creating a third suture color or striped suture. This additional color suture provides differentiation between the other suture strands and acts as a visual indicator when tying off the sutures.

The needle to double suture ratio is greater than 1:1 but does not exceed 3:1. This needle to double suture ratio is defined as the ratio of the needle wire diameter to twice the diameter of the suture. Thus, the needle is at least as large in crossection as the strands being drawn through tissue by the needle.

The suture system of the present invention results in a significant reduction and more particularly a reduction of between about forty to fifty percent (40-50%) in the number of needles and steps required to implant a prosthetic heart valve, and also reduces the time required for the procedure and the incidence of suturing errors. The suture system of the present invention provides many advantages to a surgeon. The surgeon can achieve proper spacing of the adjacent sutures which reduces the risk of peri-valvular leakage or interstitial bleeding that can occur as a result of using the interrupted sutures of the prior art. Further, there is a reduced risk for the needle to damage the adjacent suture as a result of trying to achieve the exact placement of the adjacent sutures that can occur with the interrupted suture technique. As the suture system of the present invention is provided with an alternating color such as a green and white suture strands and the option of using a third color suture positioned within the suture chain, confusion in determining which pairs of suture strands tie together is also substantially reduced. The spacing between two pledgets does not exceed 1-2 mm and more preferably, the pledgets are in abutting contact with each other.

Another preferred embodiment of the present invention includes a method to implant a valve prosthesis using the suture system of the present invention. The method begins, for example, by making a partial or full median sternotomy, thoracotomy or parasternal incision. In this embodiment, the patient is placed on a cardiopulmonary bypass so that the heart can be stopped. The diseased valve is then accessed and excised, and the prosthetic valve then sutured using the suture system of the present invention.

The method further comprises placing the first suture in the tissue using a single-stranded or armed needle. The next double-stranded needle is then taken and a second stitch is placed in the annulus of the valve site approximately 4-6 mm from where the first stitch was placed. Because the second needle is double stranded, the second stitch places the second stitch of the first suture along with the first stitch of the second suture. The following sutures are placed using the double-stranded needles, 4-6 mm from the previous suture placement until the entire circumference of the valve annulus has been sutured.

Once the entire circumference of the valve annulus has been sutured, the prosthetic valve is sutured. The prosthetic is held approximately 5 cm above the valve annulus during suturing. The sutures are placed through the cuff of the prosthetic valve using first a single-armed or stranded needle to place the first suture and then using the double-stranded needles placed through the cuff so that the pairs of sutures are evenly spaced around the circumference of the cuff. The prosthetic valve is aligned with the valve annulus. Once the sutures have been placed around the entire circumference of the cuff, the valve is lowered into position, the needles are cut off the sutures and the sutures are tied. The optional third color suture aids in tying off the sutures by acting as an additional visual indicator to differentiate between the suture strands associated with each pad or pledget. The prosthetic valve is then tested and the incision is closed.

The suture system of the present invention has different applications for many commonly performed medical procedures. For example, the suture system can be used in surgical procedures to correct ventricular aneurysms, atrial septal defects, and ventricular septal defects. Further, the suture system of the present invention can be used in procedures such as implanting of left ventricular assist devices. Aortic and mitral valve annuloplasty can also use the suture system of the present invention. In a preferred embodiment mechanical or electromechanical systems can be used in holding or manipulating the sutures during surgery.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 1 is a schematic illustration of a suture system in accordance with the present invention.

FIG. 2 is a schematic illustration of a plurality of sutures in accordance with the present invention.

DETAILED DESCRIPTION OF THE INVENTION

Figure 3A:
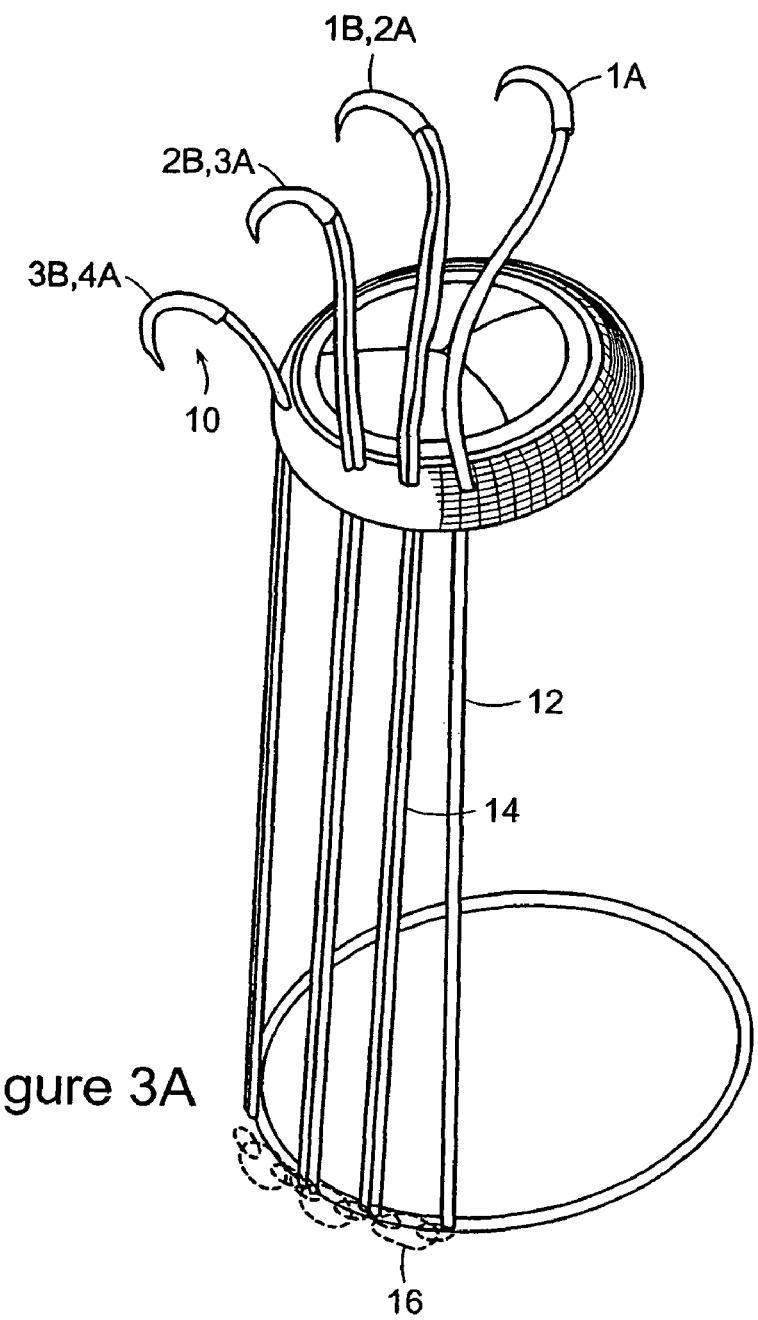
FIG. 3A is a schematic illustration of the suture system in accordance with the present invention during the implantation of a prosthetic valve.

The present invention relates to a suture system for implanting valved prostheses. Valve implantation, such as cardiac valve implantation, consists of complex suturing process. This includes the placement of multiple mattress sutures in the tissue at the valve site, as well as to the suturing ring or cuff of the valve prostheses. This procedure is complicated by a very small working space inside the arteriotomy or aortotomy in order to excise the diseased native valve, then implant the prosthetic valve. In order to prevent perivalvular leakage and proper seating of the prosthetic valve, the surgeon normally places multiple (i.e., 14 or more) double-ended, pledgeted sutures in mattress or other configuration through both the in-situ annulus of the native, removed valve, and the suturing ring or cuff of the prosthetic valve. The suture strands are made of nonabsorbable polyester and are of a fixed length with a needle attached on both ends. The pledgets are made of PTFE or similar material. The pledgets or pads are absorbent patches used to protect a wound. The pledgets are in square, rectangular, oval, circular or other shape with a pair of holes or openings through which a single suture strand passes. The size of the pledget varies with a preferred size of 4×8 mm. In the alternative, a non-pledgeted suture system can also be used with only the suture strands with a needle attached on both ends.

Because of the complex anatomy, precision needed, and small working space, valve implantation suturing is very tedious and slow. Often times, tissue locations are hidden and are difficult to access for suturing. Typically one-third of the stitches are difficult to sew with every other stitch being more difficult to sew because of tight spacing. In order to minimize the risk of perivalvular leakage, a surgeon commonly tries to place each new suture's first needle pass in the annulus and dewing ring as close to the prior suture's exit path in both structures, without actually going through the same entry and exit hole. If the suture were to pass in the same entry and exit hole, the surgeon would most likely split or impale the previous suture, which is commonly referred to as "William Tell." This may use the suture to break when it is tied or it may cause the valve to leak due to the application of unequal pressure to the valve annulus. Therefore, this occurrence would require the surgeon to remove the previous suture and start over.

The present invention suture system consists of a daisy chain of multiple pre-pledgeted mattress sutures joined at the needles. Referring to FIGS. 1 and 2, each needle 10 in the chain is attached to two strands of suture 12, 14, rather than a single strand as in the prior art. One of the strands 12 is the first of a pair, in a standard mattress suture. The other, however, is the second strand 14 of the preceding neighboring pair. Pairs are of alternating color, for example green or white, to allow for individual pairs to be differentiated at a glance. Pledgets 16 are sewn throughout the sutures. As discussed hereinabove, to ensure that the entire circumference of the prosthesis is seated in the annulus in a fluid tight fashion, multiple sutures are required. If the diameter of the tissue annulus is 29 mm, which is typical in mitral valve replacement, and the mattress sutures are placed such that each encompasses 5 mm of annulus, for example, approximately 18 discrete mattress sutures are required (29 mm×3.14/5 mm). As such, in order to place 18 pledgeted sutures the surgeon needs only to pass 20 needles, rather than 36 required by the conventional technique. A single suture system preferably uses at least three needles and can have as many needles as necessary for a given procedure. A preferred embodiment uses multiples of three in a given system such as six, nine, twelve, etc. However, the number in a given system depends upon the specific application. A given suture set can be packaged for sterile delivery and ease of use.

Furthermore, the present invention addresses the technical demands imposed by spacing requirements. The two strands that are preferably spaced as close as possible without piercing each other are now attached to the same needle. They therefore pass through the same hole in both the tissue and the prosthetic suturing ring intimately in contact with each other, with no chance of one passing around or through the interstices of the other. The net number of steps required for valve implantation is almost cut in half. In addition, the demands of obtaining close proximity without suture penetration is substantially reduced.

Referring to FIG. 3, in order to facilitate the description of this suture system, each needle, suture and pledget is labeled. As such, each suture is defined as 1, 2, 3 . . . etc., each needle 10 is identified on each suture as either 1A, 1B2A, 2B3A, 3B4A, . . . etc., and each pledget 16 is identified as being attached to its suture 1,2,3 . . . etc. The present invention suture device is a system, which consists of multiple, needles 10 which are pre-attached in either a drilled or channeled configuration to two (2) independent, pre-pledgeted or non-pledgeted sutures of alternating suture 12, 14 colors. In this configuration, the device in accordance with the present invention would be:

| Needle | Suture(s) Attached | Pledget on Suture | Color of Suture (suture #) |
|---|---|---|---|
| 1A | 1 | Yes, on 1 | Green (1) |
| 1B2A | 1 and 2 | Yes, on 1 and 2 | White (2) |
| 2B3A | 2 and 3 | Yes, on 2 and 3 | Green (3) |
| 3B4A | 3 and 4 | Yes, on 3 and 4 | White (4) |
| Etc. | | | |

Figure 3B:
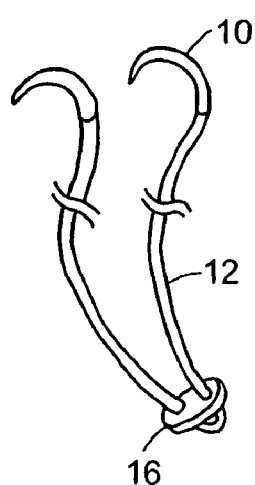
FIG. 3B is an enlarged view of a suture shown in FIG. 3A.

This suture system allows approximately half (50%) as many needle 10 passes by combining two sutures 12, 14 to one needle. This also allows for both sutures to fill the same entry and exit holes in the annulus and suturing ring without splitting, or impaling one another. This suture configuration allows optimal seating of the valve without perivalvular leakage. The time for implantation is also dramatically reduced. FIG. 3B is an enlarged view showing the pledget 16 on suture 12. The pre-pledgeted sutures can be packaged for delivering continuously attached valve sutures in a holder for either manual or mechanically aided delivery.

Figure 4:
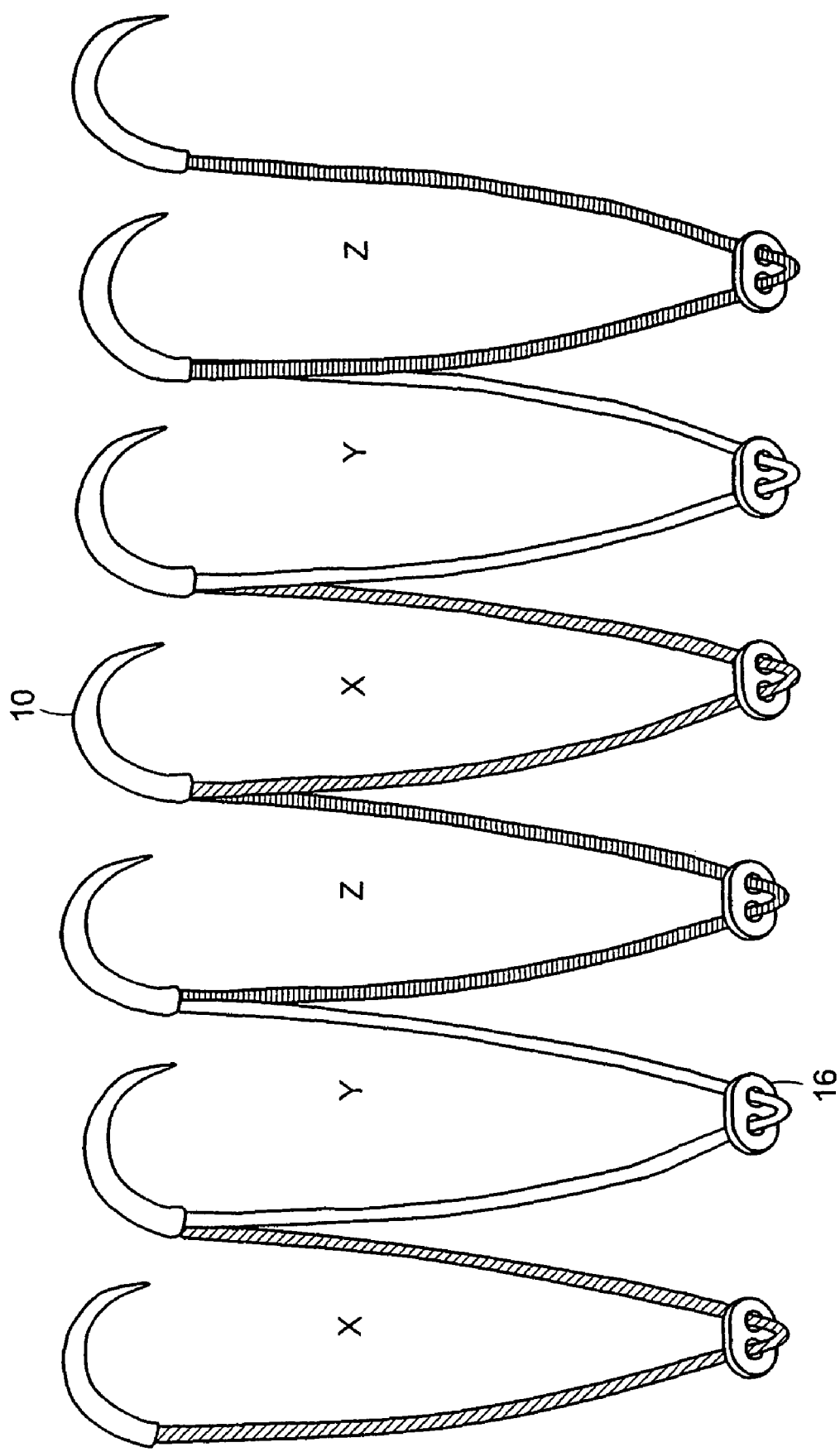
FIG. 4 is a schematic illustration of a preferred embodiment of the suture system in accordance with the present invention.
Figure 5:
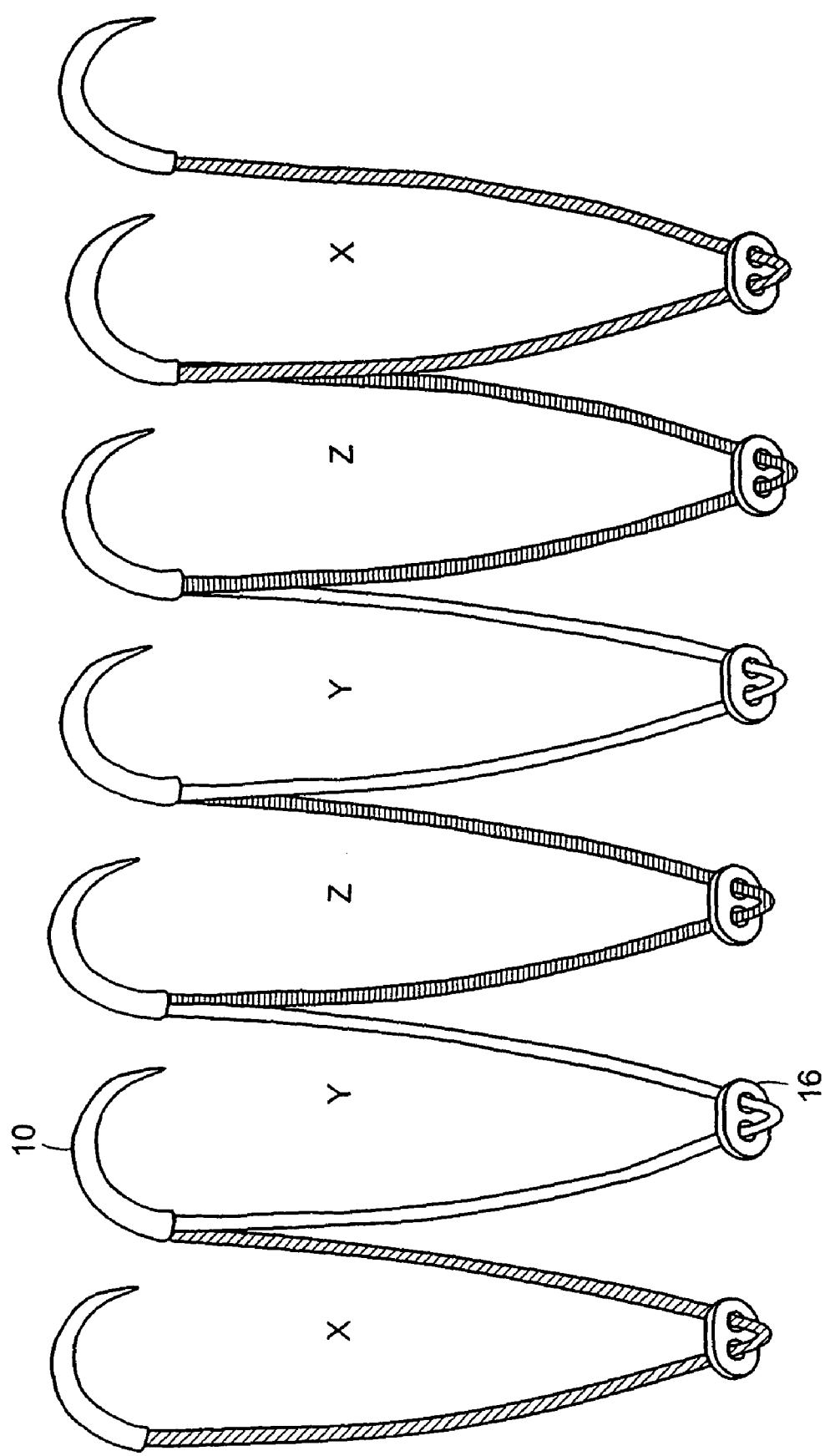
FIG. 5 is a schematic illustration of another preferred embodiment of the suture system in accordance with the present invention.

Referring to FIGS. 4 and 5, the suture system of the present invention contains three different colors, x, y, and z of suture and shows 6 sutures. The three colors may alternate sequentially or a third color may be utilized in one or both of the end positions of the strand.

When using two colors of suture, for example X and Y, every hole contains both color of suture. Therefore, after the needle 10 has been removed, some confusion can arise as to whether to tie a particular suture to the matching color from the hole on one side or the other of the selected suture. This confusion can also arise at the junction between two different strands of product. Although there are techniques that will enable the surgeon to make a correct determination when tying, the three-color embodiment negates the need for such techniques.

The three-color embodiment facilitates identification of the end of the sutures which must be tied together during the tying process. This facilitation is due to the fact that the color combination of the two sutures in any given hole will be different from the two colors in the two adjacent holes. For example, the color combination in a sequence of holes with suture colors X, Y and Z would be XY, YZ, ZX, XY, YZ, ZX, etc. The three colors make it easier to determine which end of the suture to tie together as there is only one matching suture in the two adjacent holes.

Figure 6:
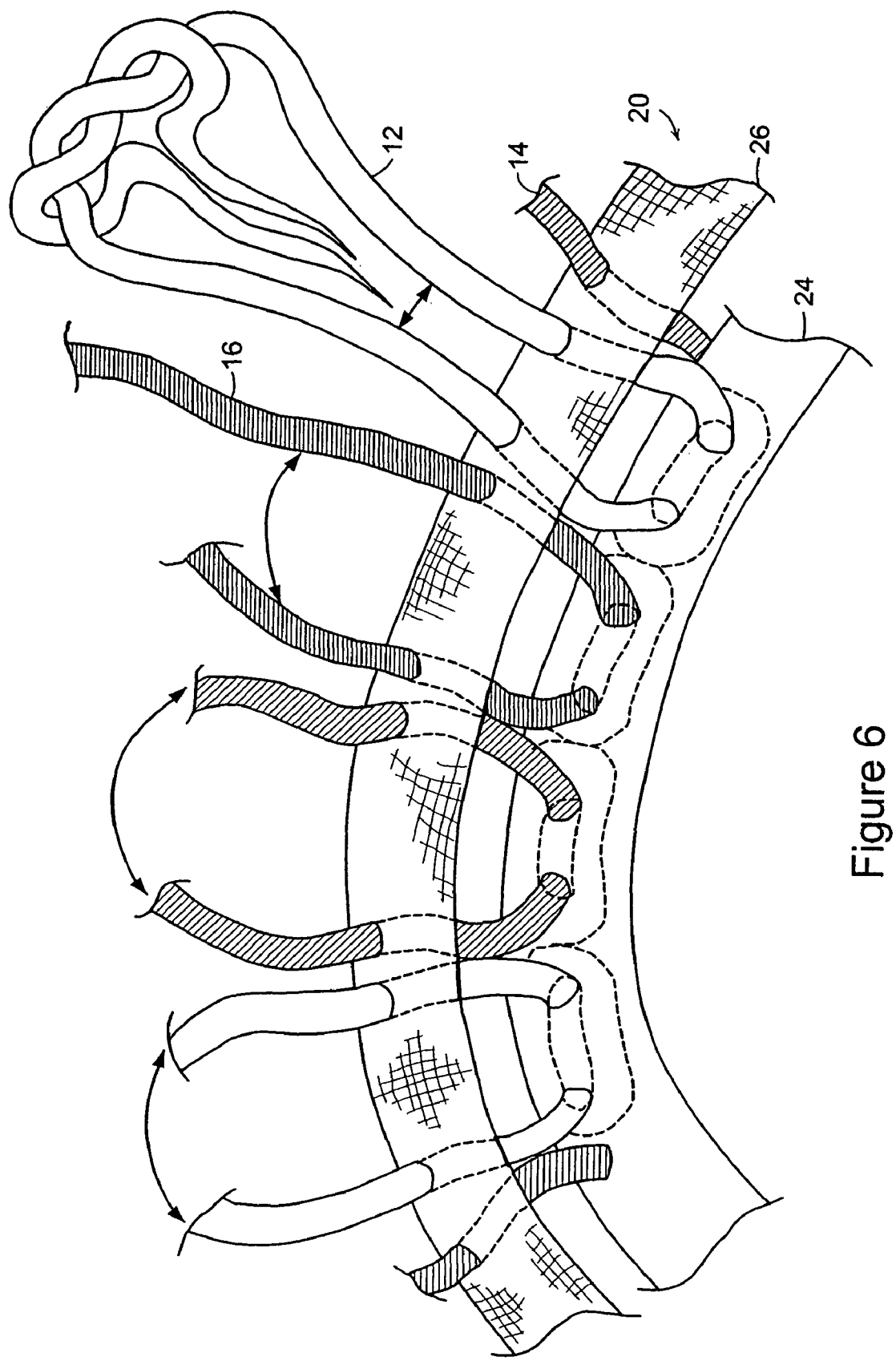
FIG. 6 is a schematic illustration of an embodiment of the suture system of the present invention including three-color sutures.

FIG. 6 illustrates a prosthetic valve 20 being implanted using the three color embodiment of the suture system of the present invention. Note that the valve can have a pair of hinged flaps that are free to rotate between open and closed position. The valve annulus 24 is first sutured along the entire circumference. The prosthetic valve 20 is then sutured along the entire circumference of the cuff 26. The double-stranded needles place the second stitch of the first suture along with the first stitch of the second suture for example. This requires only one needle pass. The two strands are thus as close as possible without piercing each other. The prosthetic valve 20 is aligned with the valve annulus 24 while suturing. Once the sutures 12, 14, 16 have been placed, the needles are cut off the sutures and the sutures are tied. Adjacent like color sutures are tied together as illustrated in FIG. 6. The third color suture aids in tying off the sutures by acting as an additional visual indicator to differentiate between the adjacent sutures. The pledgets are placed in an abutting relationship or at a distance from each other depending on the circumstances of each patient. The entire circumference of the prosthesis 20 is seated in the annulus 24 with the pledgets 16 and the tightly tied sutures 12, 14, 16 aiding in preventing leakage between the prosthetic valve 20 and the valve tissue annulus 24.

Figure 7:
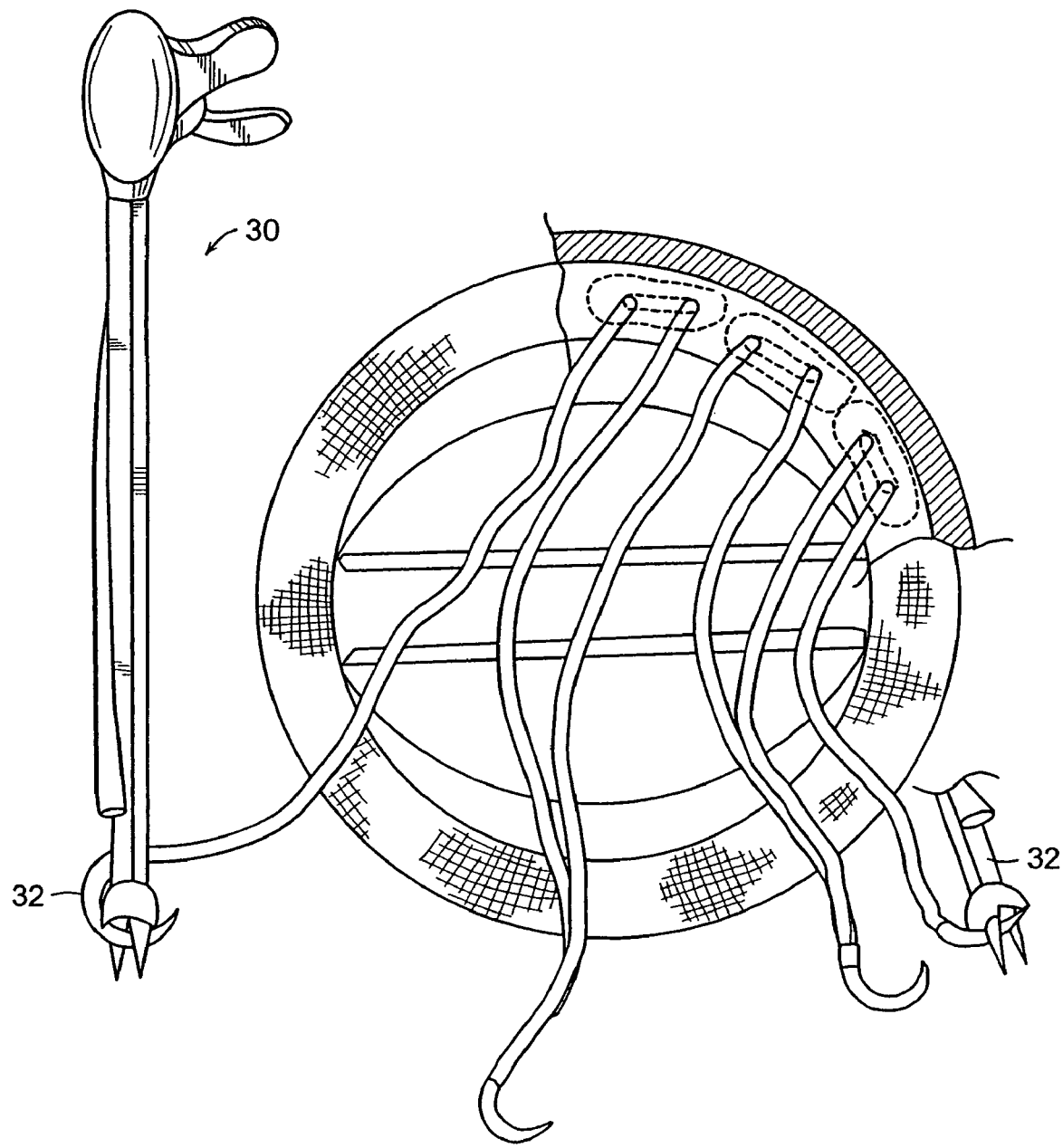
FIG. 7 is a schematic illustration of the suture system being used in a mitral valve replacement procedure including an automated robotic apparatus in accordance with the present invention.

A number of devices have been proposed for automating the process of suture placement to facilitate valve replacement. A device that takes advantage of the present invention daisy chain configuration has a significant advantage due to increased tolerances with respect to suture spacing. As such, the invention as stated is an important integral part of an automated valve implantation device. FIG. 7 illustrates a handheld mechanical automated or robotic placement device 30 that can be used with the suture system of the present invention. A robotic system including a pair of robotic arms 32 assists the suturing system of the present invention. The robotic arms 32 can be manipulated to hold and suture the prosthetic valve 20 to the valve annulus tissue 24 with tight space tolerances. The movement of the robotic arms are controlled by the surgeon who can have an optically magnified view of the valve annulus where the prosthetic valve is being implanted. In an alternative embodiment, a camera can assist the surgeon in viewing the area where the prosthetic valve is being implanted. Methods and apparatus for performing minimally invasive cardiac procedures are disclosed in U.S. Pat. Nos. 5,855,583, 5,911,036, 5,762,458, 5,807,377, 5,797,900 and 5,792,135, the entire contents of these patents being incorporated herein by reference.

Figure 8:
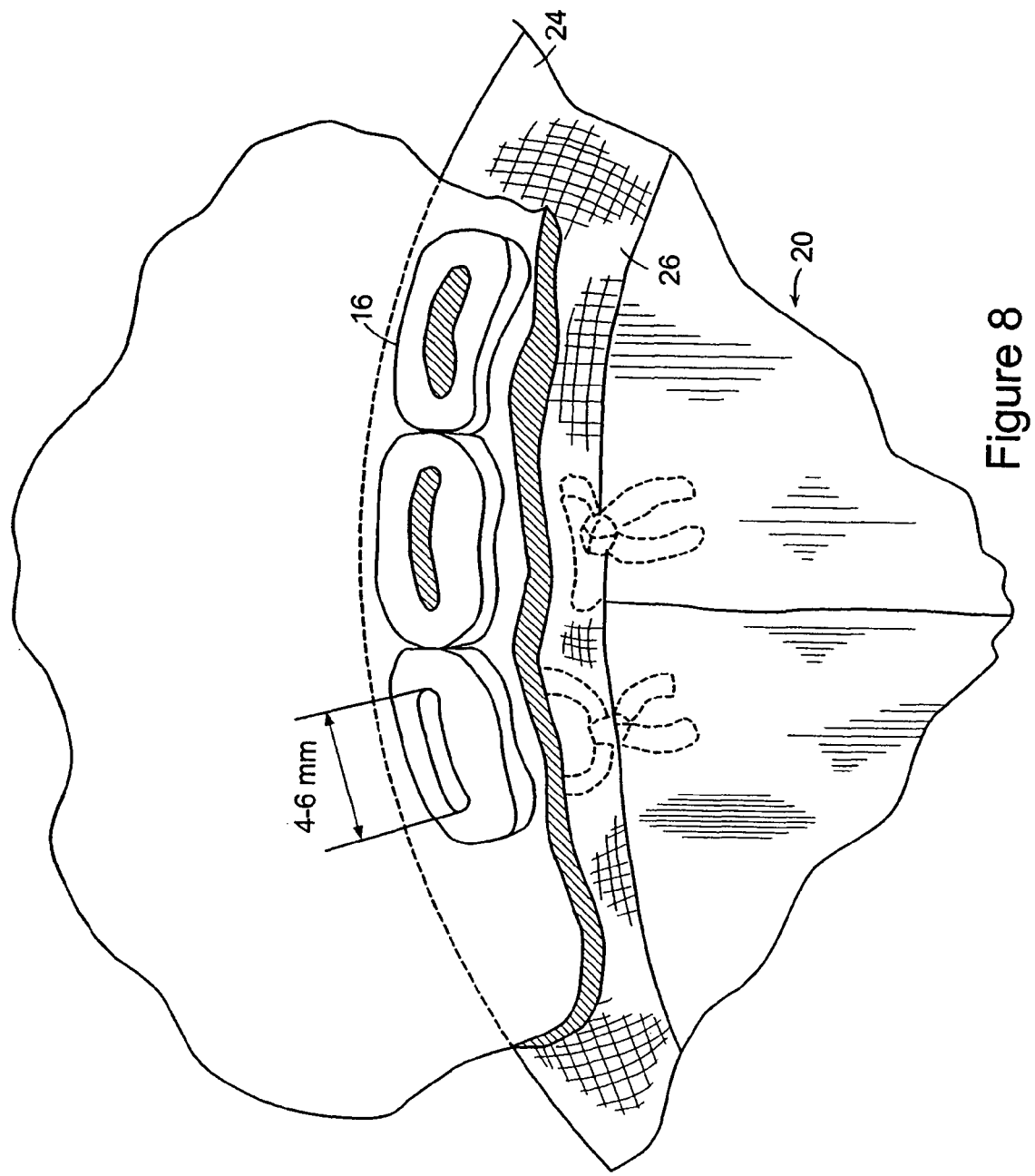
FIG. 8 is an enlarged view illustrating the pledgets of the suture system as they are sutured during valve replacement surgery.

FIG. 8 illustrates the pledgets 16 sutured to the valve annulus tissue 24. The entire circumference of the valve annulus tissue 24 has pledgets 16 sutured thereto. The sutures are tied to the cuff 26 of the prosthetic valve 20 after the prosthetic valve 20 is aligned with the valve annulus 24 and sutured thereto.

Figure 9:
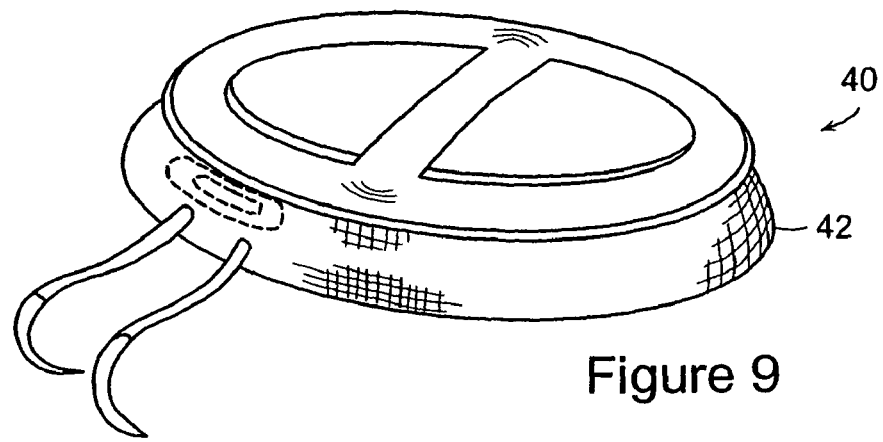
FIG. 9 is a schematic illustration of a prosthetic heart valve being secured using the suture system of the present invention.
Figure 10:
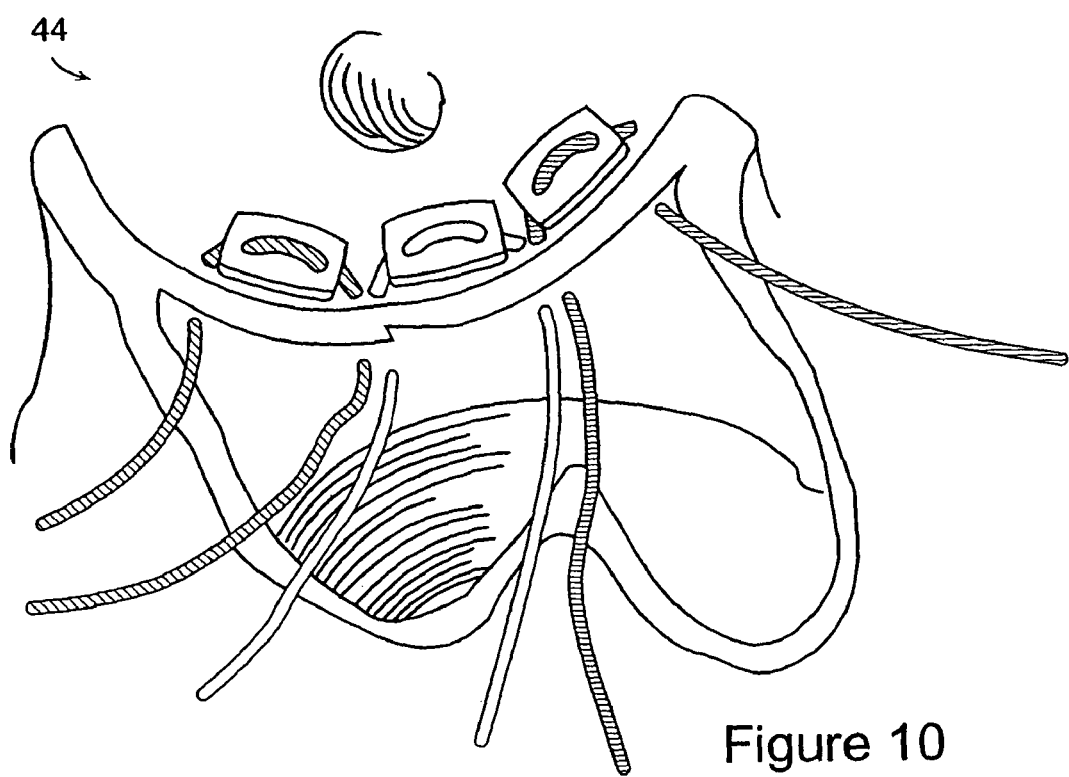
FIG. 10 is a schematic illustration of an aortic valve being secured using the suture system according to the present invention.

FIG. 9 illustrates a mitral prosthetic valve 40 having a suturing cuff 42. The sutures are stitched around the circumference of the cuff 42. FIG. 10 illustrates an aortic valve suturing process for implanting an aortic prosthetic valve using the suturing system of the present invention.

Figure 11:
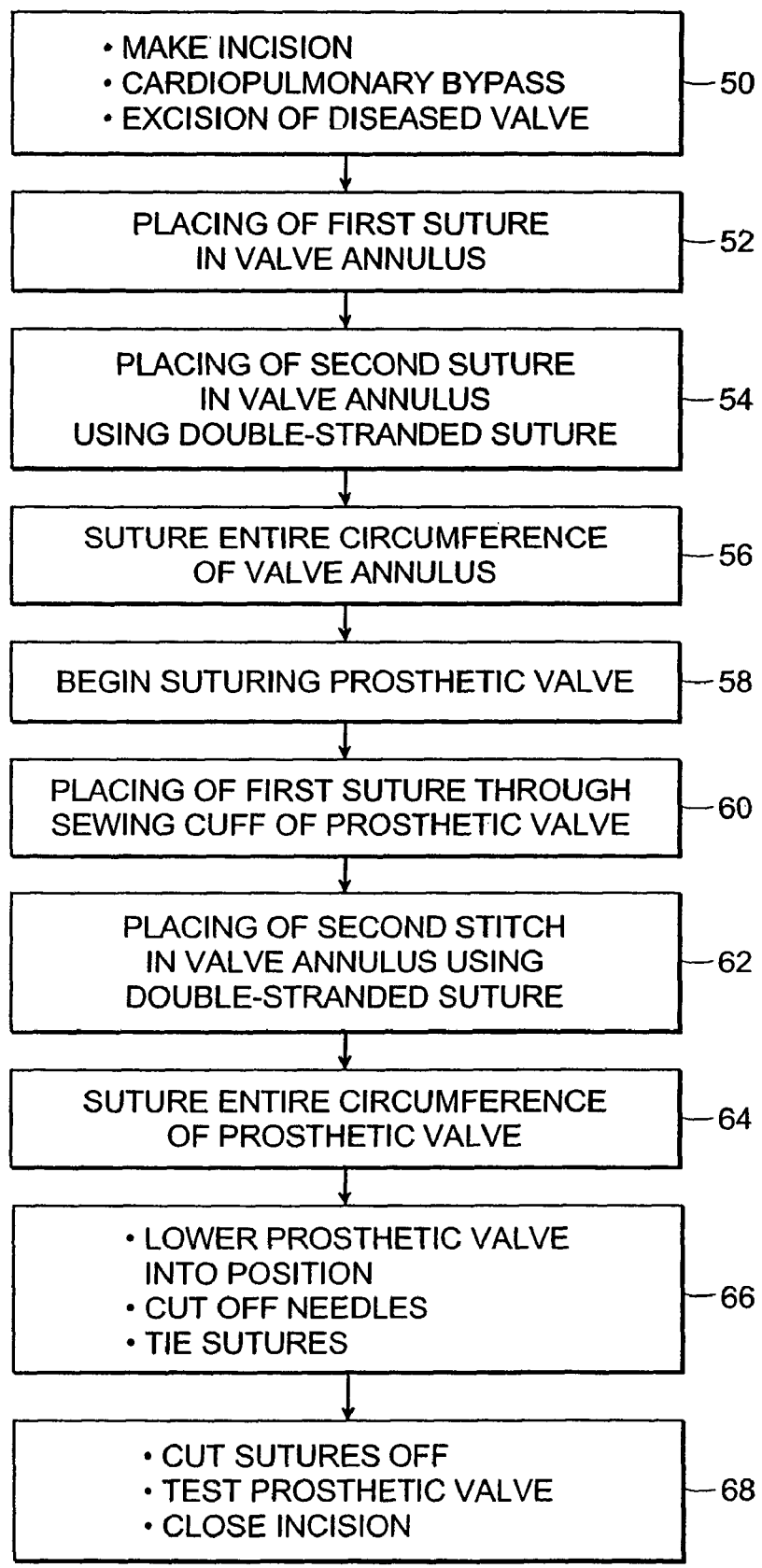
FIG. 11 is a flowchart of a method for performing a valve prosthesis using the suture system in accordance with the present invention.

The method for performing the implantation of a valve prosthesis using the suture system of the present invention is illustrated in FIG. 11 and begins in step 50 by making a partial or full median sternotomy, thoracotomy, or parastemal incision. The patient is then placed on cardiopulmonary bypass so that the heart can be stopped. Once the diseased valve is accessed, it is excised and the valve annulus is sized to insure proper fit of the new prosthetic valve. The prosthetic valve is then sutured in place after the suture size and needle type are selected according to surgeon preference. The suture system and method of the present invention further includes a particular sequence of steps. In step 52, the surgeon places the first suture in the tissue annulus using either of the single-armed ends of the suture chain. Next in step 54, the surgeon takes the next double-stranded suture and places the second stitch in the annulus approximately 4-6 mm from where the first stitch was placed. Because the second needle is double-stranded, the second stitch places the second stitch of the first suture along with the first stitch of the second suture. This requires only one needle pass as compared to two needle passes required with interrupted sutures and there is exact placement of the adjacent suture. In step 56, the surgeon continues placing the sutures using the double armed needles, 4-6 mm from the previous suture placement, until the entire circumference of the valve annulus has been sutured. Again, the needles are double-stranded, thus placing the second stitch of one suture with the first stitch of the next suture with only one needle pass. This reduces the number of needle passes almost in half of the two needle passes required for each suture when using the interrupted suture technique.

In this particular embodiment as illustrated in step 58, once the entire circumference of the tissue annulus has been sutured, the surgeon begins suturing the prosthetic valve. The prosthetic valve is held approximately 5 cm above the valve annulus during suturing. The surgeon, per step 60, takes one of the single-armed needles and places the first suture through the cuff of the prosthetic valve. Then per step 62, the surgeon, continues sewing through the cuff of the prosthetic valve by taking the next double-stranded needle and placing it through the cuff, at a distance from the previous needle's position such that the pairs of strands will be evenly spaced around the cuff. Note that with only one stitch of the double-stranded needle, the second stitch of the first suture along with the first stitch of the second suture is place. This requires two needle passes when using interrupted sutures. Also, there is exact placement of the adjacent suture. In step 64, the surgeon continues sewing through the cuff of the prosthetic valve using the double-stranded needles. The surgeon places each double-stranded needle through the sewing cuff of the prosthetic valve at a known distance mm from the previous suture placement, until the entire circumference of the valve annulus has been sutured. Careful attention is paid to the alignment of the prosthetic valve to the valve annulus. Again, the needles are double-stranded, thus placing the second stitch of one suture with the first stitch of the next suture with only one needle pass. This reduces the number of needle passes almost in half of the two needle passes required for each suture when using interrupted suture.

Per step 66, once the sutures have been placed around the entire circumference of the cuff, the valve is lowered into position, the needles are cut off the sutures and the tying of the sutures begins. The optional third color suture can aid in typing off the sutures by acting as an additional visual indicator to differentiate between the sutures. Then, per step 68, the surgeon removes the excess strand material. The valve is tested to insure unimpaired opening and closing and the incision is closed.

The present invention further includes a valve suture packaging system for delivering continuously attached sutures in a compact holder. The packaging (carrier) design enables the sutures to be used directly from the package at a location close to the surgical incision. The carrier is a compact folder which holds multiple continuously attached sutures. The carrier top flap folds back forming a convenient handle which prevents the package from being compressed, restricting delivery of the sutures. Each suture is separately threaded through holes in the holder preventing the sutures from tangling during removal from the carrier. The structural design has folding panels permitting flexibility to utilize the holder for different suture lengths. Needles are delivered extended from the package providing easy access, and are affixed in a foam strip for needle point protection. Pledgets are positioned above the foam to prevent catching and tangling.

While this invention has been particularly shown and described with references to preferred embodiments thereof, it will be understood by those skilled in the art that various changes in form and details may be made therein without departing from the spirit and scope of the invention as defined by the appended claims.

What is claimed:

1. A method for implanting a prosthetic device in a body comprising:
   placing a first suture strand through tissue at a first position using a first needle of a suture system having more than three needles connected by suture strands;
   placing a second needle of the suture system in the tissue at a distance from the first position, the second needle being attached to the first suture strand and a second suture strand having different indicators such that the first strand and the second strand can be identified, the second needle having a needle diameter at least as large as the diameter of the first suture strand added to the diameter of the second suture strand;
   placing additional sutures using additional needles attached to the second needle through the tissue;
   using more than three needles to insert the suture strands through the prosthetic device; and
   using the suture strands having the indicators to secure the prosthetic device into position.

2. The method of claim 1 wherein the first and second suture strands are of different colors.

3. The method of claim 2 wherein a third strand color is formed with a pair of braided strands of different colors.

4. The method of claim 1 wherein the first suture strand is green and the second suture strand is white.

5. The method of claim 1 further comprising threading the suture strands through a cuff of the prosthetic device.

6. The method of claim 5 wherein the threading step comprises inserting the suture strands through an annular cuff, the suture strands extending around a central valve.

7. The method of claim 1 further comprising providing one or more suture pads that are attached to the suture strands.

8. The method of claim 1 further comprising passing the suture strands through a cuff of the prosthetic device.

9. The method of claim 1 further comprising passing the different strands attached to the second needle through a hole in the tissue at a second position, the second needle having a diameter larger then the strands that are attached to the second needle such that the strands attached to the second needle fit within the hole in the tissue.

10. The method of claim 1 wherein the prosthetic device comprises a valve.

11. The method of claim 1 further comprising providing the suture system in a package.

12. The method of claim 1 wherein the needles of the suture system are attached by suture strands with alternating colors.

13. The method of claim 1 further comprising using strands having at least three different colors to connect the needles in sequence.

14. The method of claim 1 further comprising using pairs strands from different holes having identified indicators to secure the device.

15. A suture device for suturing a prosthetic heart valve to tissue comprising:
a plurality of more than three connected needles, one of the plurality of needles being a first double stranded needle attached to a first suture strand and a second suture strand, at least said first suture strand having a visual indicator to distinguish the first suture strand from the second suture strand;
the plurality of more than three connected needles including a first end needle attached to a first single suture strand and a second end needle attached to a second single suture strand and further comprising a second double stranded needle attached to an end of the second suture strand and an end of a third suture strand;
each suture strand extending between a pair of the connected needles such that suture strands attached to one of the plurality of needles can be distinguished with a visual indicator, the needles being removable from the suture strands after insertion through a cuff of a heart valve and the ends of each strand being identified and secured with another identified strand to attach the device to the tissue.

16. The suture device of claim 15 wherein the suture strands include strands of at least two different colors.

17. The suture device of claim 15 wherein the device has at least three needles that are each associated with at least two strands.

18. The suture device of claim 15 further comprising a plurality of suture pads such that each needle is attached to another needle with a suture strand having a pad attached to the suture strand, the suture pads defining the spacing between adjacent needle holes in the cuff of the heart valve.

19. The suture device of claim 15 further comprising a package for housing the suture device, the package having at least six needles.

20. The suture device of claim 15 further comprising a mechanical suture placement device.

21. The suture device of claim 15 wherein the suture device is configured for suturing a prosthetic aortic valve.

22. A method for implanting a heart valve in a body comprising:
inserting a first suture strand through tissue at a first position using a first needle of a suture system having at least three needles connected by suture strands;
inserting a second needle of the suture system, the second needle being attached to the first suture strand and a second suture strand, through the tissue at a distance from the first position, the first suture strand and the second suture strand having different indicators such that the different strands attached to the second needle can be identified, the second needle having a diameter larger then the first suture strand and the second suture strand that are attached to the second needle;
inserting a third needle of the suture system through tissue, the third needle being attached to the second suture strand and a third suture strand;
inserting a fourth needle of the suture system through the tissue, the fourth needle being attached to the third suture strand; and
attaching a cuff of the heart valve device to the tissue using the strands having the indicators.

23. The method of claim 22 wherein the first suture strand and the second suture strand are of different colors.

24. The method of claim 22 wherein the suture system has at least two double stranded needles attached to pairs of different colored strands.

25. The method of claim 22 wherein the system has at least six needles connected by suture strands.

26. The method of claim 22 wherein the step of inserting the second needle further comprises inserting the second needle through a single hole in the tissue such that the suture strands attached to the second needle extend through the single hole.

27. The method of claim 26 further comprising using the indicators to identify the strands extending through the single hole and select strands from adjacent holes in the tissue to secure the identified strands.

28. A suture device for suturing a prosthetic device to tissue comprising:
a plurality of at least seven needles connected by a plurality of at least six suture strands such that pairs of the suture strands attached to at least five of the needles have a visual indicator to distinguish the pairs of suture strands attached to each of the at least five needles, the ends of each pair of suture strands being inserted into one of the at least five needles.

29. The suture device of claim 28 wherein the suture strands include strands of at least two different colors.

30. The suture device of claim 28 wherein the device has at least one braided suture using two suture strands having different colors.

31. The suture device of claim 28 further comprising a first needle attached to a first single suture strand and a last needle attached to a second single suture strand.

32. The suture device of claim 28 wherein the at least six suture strands further comprise a first strand of a first color, a second strand of a second color different from the first color and a third strand of a third color that is different from the first color and the second color.

33. The suture device of claim 32 wherein the third color comprises a strand of the first color braided with a strand of the second color.

34. The suture device of claim 28 wherein at least one of the needles has a diameter larger than a diameter of the pair of strands attached to the at least one needle.

* * * * *